US008899240B2

(12) United States Patent
Mass

(10) Patent No.: US 8,899,240 B2
(45) Date of Patent: Dec. 2, 2014

(54) ELECTRIC SUBSTITUTE CIGARETTE

(76) Inventor: Bernard Karel Mass, Hamont (BE)

( * ) Notice: Subject to any disclaimer, the term of this patent is extended or adjusted under 35 U.S.C. 154(b) by 1010 days.

(21) Appl. No.: 13/125,274

(22) PCT Filed: Jun. 27, 2008

(86) PCT No.: PCT/CN2008/001240
§ 371 (c)(1), (2), (4) Date: Apr. 20, 2011

(87) PCT Pub. No.: WO2009/155734
PCT Pub. Date: Dec. 30, 2009

(65) Prior Publication Data

US 2011/0232654 A1 Sep. 29, 2011

(51) Int. Cl.
*A24F 47/00* (2006.01)
*A61M 15/06* (2006.01)

(52) U.S. Cl.
CPC .............. *A61M 15/06* (2013.01); *A24F 47/008* (2013.01); *A61M 2205/8206* (2013.01)
USPC ............................ 131/273; 131/270; 131/194

(58) Field of Classification Search
CPC ... A24F 47/002; A24F 47/004; A24F 47/008; A24B 15/165; A61M 2205/8206
USPC ...................... 131/270–273, 194; 128/202.21
See application file for complete search history.

(56) References Cited

U.S. PATENT DOCUMENTS 4,765,347 A * 8/1988 Sensabaugh et al. ......... 131/273
4,945,931 A * 8/1990 Gori .............................. 131/335
5,042,510 A * 8/1991 Curtiss et al. ................ 131/273
5,060,671 A * 10/1991 Counts et al. ................ 131/329
5,249,586 A * 10/1993 Morgan et al. ................ 131/194
7,015,796 B2 * 3/2006 Snyder ..................... 340/309.16
7,832,410 B2 * 11/2010 Hon .............................. 131/273
2007/0267031 A1 * 11/2007 Hon .............................. 131/273
2008/0092912 A1 * 4/2008 Robinson et al. ............. 131/200
2009/0188490 A1 * 7/2009 Han ......................... 128/200.14
2012/0090630 A1 * 4/2012 Hon .............................. 131/273

FOREIGN PATENT DOCUMENTS

EP 0845220 * 6/1998 .............. A24F 47/00
EP 1618803 A1 * 1/2006 ............. A24B 15/16
EP 1618803 * 9/2007
GB 2466758 A * 7/2010 ............. A24F 47/00
WO WO 2005099494 A1 * 10/2005

* cited by examiner

*Primary Examiner* — Richard Crispino
*Assistant Examiner* — Yana B Krinker
(74) *Attorney, Agent, or Firm* — Shimokaji & Associates P.C.

(57) ABSTRACT

An electronic substitute cigarette includes a cigarette rod(10) and a simulated cigarette mouthpiece(20). Said cigarette rod (10) includes a power source and an electronic circuit. Said simulated cigarette mouthpiece(20) includes a simulated filter(25), a liquid storage chamber(28) and an atomizer(22). The atomizer(22) is connected with the power output terminal of the cigarette rod(10). A columnar alloy sponge is mounted within the atomizer(22). The simulated filter(25) includes a main body(252) and a through hole(254). The liquid chamber (28) mounted into one end of the through hole(254) includes a container(281) having at least one protrusions(284) and a sealing membrane(30). While the simulated filter(25) with the liquid chamber(28) is engaged with the atomizer(22), the sealing membrane(30) is broken by the columnar alloy sponge, the liquid in the container (281) leaks out and gets into the columnar alloy sponge and then is atomized by the atomizer(22), then gases or smoke flows into space between the protrusions(284) and the simulated filter(25) and gets into the mouth of the user.

16 Claims, 3 Drawing Sheets

22
25
252
254
28
287
288

ELECTRIC SUBSTITUTE CIGARETTE

BACKGROUND OF THE INVENTION

1. Field of the Invention

The present invention relates to an electronic substitute cigarette, particularly to an electronic substitute cigarette with profile similar to a real cigarette, which can give user a true tactility like conventional smoking.

2. Background

Although it has become a common sense that smoking is harmful to the health. Statistics show that every year as much as several millions people die from smoking. However, there are still about one billion users in the world and the number is continuously expanding.

Nicotine is the major active ingredient in the cigarette, which can produce a large amount of tar mist accompanied by the combustion of cigarette in case of smoking. Such tar mist coming into the pulmonary alveoli shall be quickly absorbed to produce a sense of euphoria similar to stimulant, and thus make the smoker addicted. Therefore, it is extremely difficult for smokers to quit smoking even though smoking may incur serious respiratory diseases and cancer.

Nicotine is the alkaloid of small molecule. In small dosage it hardly does harm to the health, of which, half-life inside the blood is extremely short. Tar is the major harmful substance as produced by combustion of the tobacco, which is composed of hundreds of ingredients, including dozens of carcinogens. Therefore, many cigarette substitutes containing nicotine but tar have emerged, such as "nicotine patch", "nicotine mouthwash", "nicotine gum" and "nicotine beverage". Most of such substitutes are made of pure nicotine. As such products fail to cater to actual smoking habitants of smokers, they are unlikely to become the smoking-quit products or cigarette substitutes in real means although they are hazards as brought forth by the tar.

In view of the issues, some substitute cigarettes normally including mouthpiece, battery, liquid chamber and atomizer are provided in the prior arts, such as e-smoking device. User sucks the electronic smoking device through a mouthpiece, the battery electrifies the electronic smoking device, then the liquid in the liquid chamber flows into the atomizing chamber for atomization and gives off the aerosol out of the mouthpiece, this electronic smoking device doesn't generate tar and other hazard substances, so as not to be harmful to your health; but it also let user has the excited feeling like smoking, it can be used to help user to give up smoking and also be used for user to suck in no-smoking sites. However, as shown in International Patent Application No. PCT/CN2005/000337, the dimension of the electronic cigarette integrated with circuit panel, atomizer and liquid chamber is obviously larger than that of traditional cigarette. Furthermore, the traditional cigarette holder adopts plastic simulated cigarette mouthpiece, and this kind of mouthpiece is made of hard plastic, be short of true feeling of smoking.

SUMMARY OF THE INVENTION

An objective of the present invention is to provide an electronic substitute cigarette with profile similar to a real cigarette, which can give user a true tactility like conventional smoking, and its filter mouthpiece is replaceable and hygienic for use.

Technical proposal for settlement of the technical problems is provided in the present invention as follows: an electronic substitute cigarette includes a cigarette rod and a simulated cigarette mouthpiece. The said cigarette rod includes power source and electronic circuit. The said simulated cigarette mouthpiece includes a simulated filter, a liquid chamber and an atomizer. The atomizer is connected with the power output terminal of the cigarette rod. A columnar alloy sponge is mounted within the atomizer. The simulated filter includes a main body and a through hole. The liquid chamber mounted into one end of the through hole includes a container having at least one protrusions and a sealing membrane. While the simulated filter with the liquid chamber is engaged with the atomizer, the sealing membrane is broken by the columnar alloy sponge, liquid in the container leaks out and gets into the Columnar alloy sponge and then is atomized by the atomizer, then gases or smoke flows into space between the protrusions and the simulated filter, and gets into mouth of the user.

Electronic substitute cigarettes in accordance with the present invention integrate atomizer and liquid chamber in the simulated filter, of which, dimension and profile are similar to that of the true cigarette. It can increase the true tactility like conventional smoking and gives user a feeling of smoking true cigarette. User can control the smoking frequency through capacity control function of the liquid chamber. Furthermore, the simulated filter of this invention can be replaced at any moment, for hygienic purposes and cleanness.

DETAILED DESCRIPTION OF THE INVENTION

A detailed description for the invention will be given below in combination with the attached figures.

Figure 1:
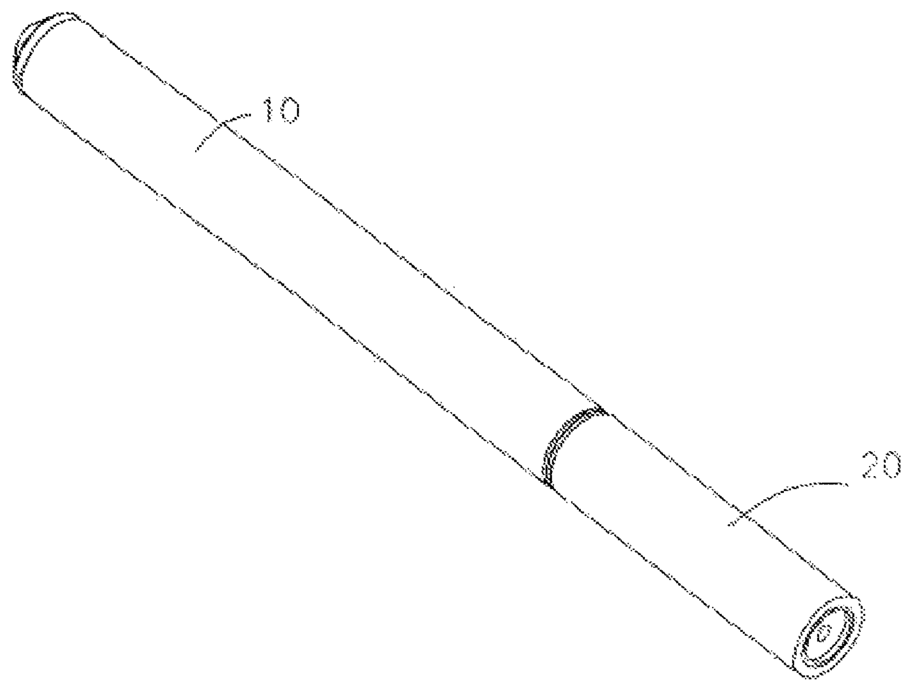
FIG. 1 is an overall structural diagram of an electronic substitute cigarette in accordance with the present invention.
Figure 2:
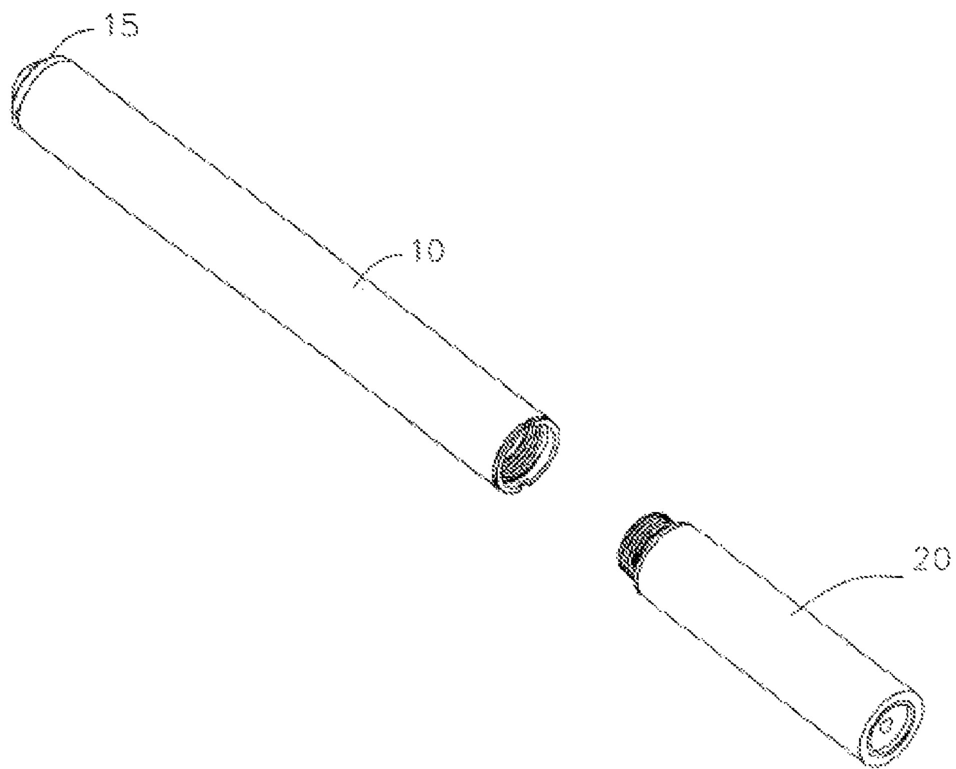
FIG. 2 is an exploded structure diagram of an electronic substitute cigarette in accordance with the present invention, which includes a cigarette rod and a simulated cigarette mouthpiece.

Referring to FIGS. 1 and 2, an electronic substitute cigarette in accordance with the present invention comprises a cigarette rod 10 and a simulated cigarette mouthpiece 20. Battery and electronic circuit are mounted within the cigarette rod 10. Generally, cigarette rod is made of plastic or similar materials. One end of the cigarette rod 10 is installed with a firelight simulating device 15. The simulated cigarette mouthpiece 20 is assembled onto a power output terminal of the cigarette rod 10. When the electronic substitute cigarette is electrified and then enters into working state, air floe with gases or smoke atomized by an atomizer 22 will flow into the mouth of user within the simulated cigarette mouthpiece 20.

Figure 3:
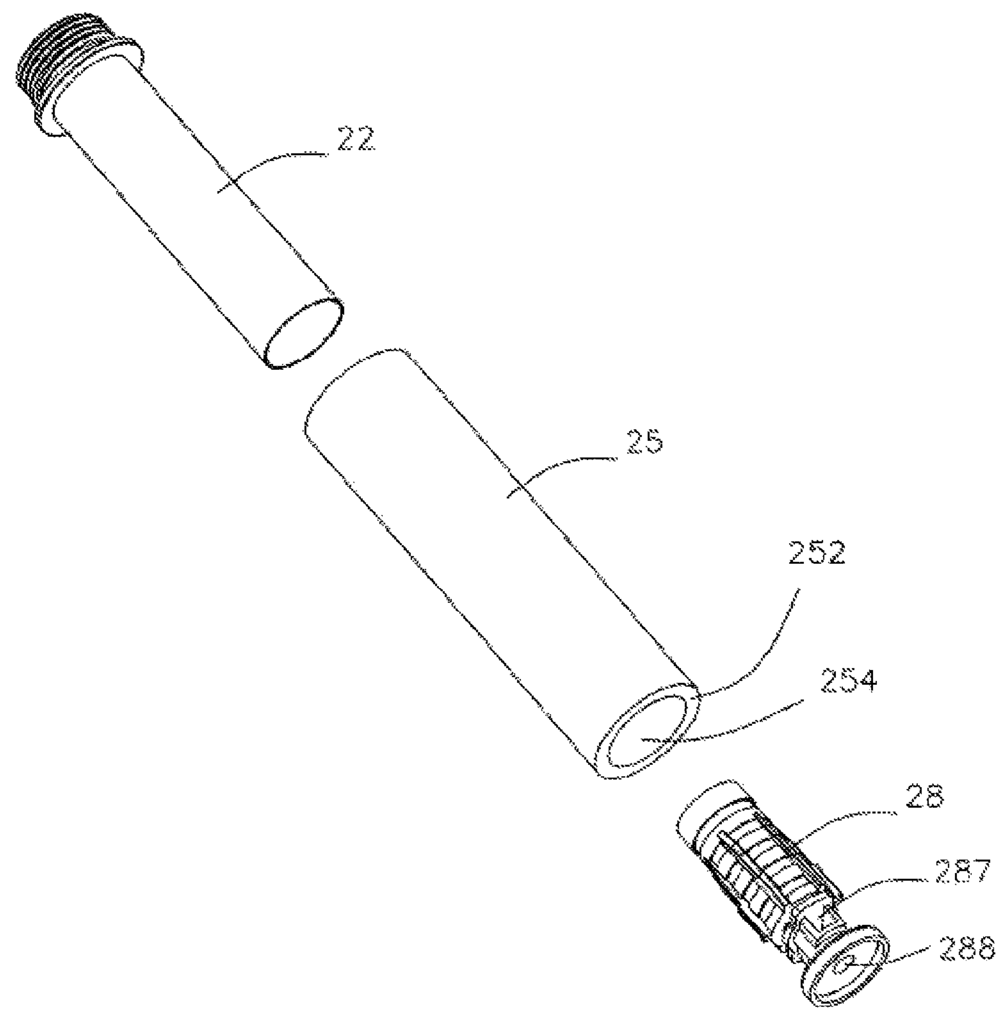
FIG. 3 is an exploded structure diagram of the simulated cigarette mouthpiece of the electronic substitute cigarette shown in FIG. 2, which includes an atomizer, a simulated filter and a liquid chamber.

Referring to FIG. 3, the simulated cigarette mouthpiece 20 comprises an atomizer 22, a simulated filter 25 and a liquid chamber 28. The simulated filter 25 comprises a cylindrical main body 252 and a through hole 254 that runs through the axes of the main body 252. The liquid chamber 28 is integrated inside the through hole 254 in the simulated filter 25. The simulated filter 25 is not used as a real filter. The main body 252 of the simulated filter 25 can be formed by making an inner hollow within a real filter mouthpiece, which is conventionally made of common man made fiber material or filler of soft sponge structure covered with common real cigarette filter paper. In other embodiments, the simulated filter 25 can be made by rolling paper and filling soft materials such as fiber, cotton and sponge structure within it. It is not provided with filter function as there is no or very little smoke passing through it. Its major function is to marking true tactility like conventional smoking and gives user a feeling of smoking true cigarette.

Figure 4:
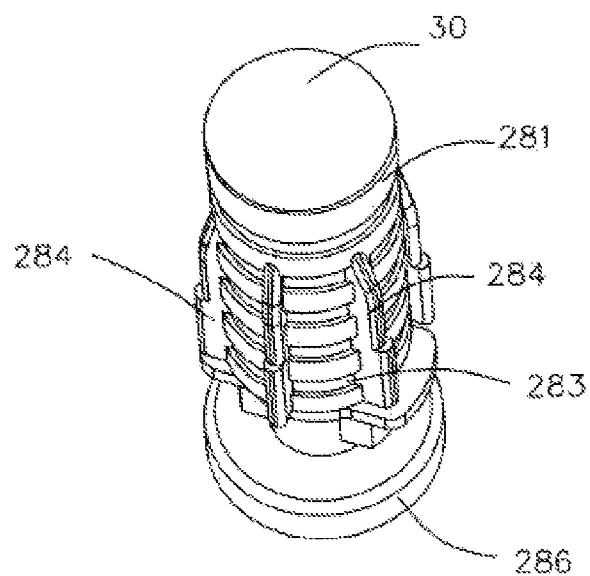
FIG. 4 is a structural diagram of the liquid chamber as shown in FIG. 3.

Further referring to FIGS. 3 and 4 together, the liquid chamber 28 comprises a container 281, a sealing membrane 30 and a base 286. The liquid chamber 28 and its sealing membrane 30 are made of such non-rigid materials as PE, PC or PU. Profile of the liquid chamber 28 matches that of the through hole 254 of the simulated filter 25. The shape of the container 281 of the liquid chamber 28 is corresponding to the through hole 254. The liquid chamber 28 is engaged with the simulated filter 25. In this embodiment, the liquid chamber 28 is in cylindrical form, which is available for perfusion of 0.05 ml-1.00 ml liquid. A plurality of grooves 283 parallel to transverse section of the container 281 is designed in its sidewall for preventing liquid rapidly formed by cooled atomized gas or smoke from leaking out along its sidewall. A plurality of protrusions 284 is extended from the sidewall of the container 281. Each protrusion 284 comprises a broader portion and a narrower portion. The broader portion of each protrusion 284 supports against the interior wall of the simulated filter 25 while the liquid chamber 28 is nested into one end of the through hole 254 of the simulated filter 25, then the liquid chamber 28 is engaged with the simulated filter 25 tightly. Meanwhile, spaces are achieved between the protrusions 284 and simulated filter 25 to let air and gases or smoke overpass successfully.

The base 286 comprises a support portion and a plate. The plate is engaged into the tail end of the through hole 254. A pair of square venthole 287 is designed in the support portion. A round opening 288 is designed in the center of the plate. The square venthole 287 and the round opening 288 are connected each other in order to let gases or smoke pass through successfully. Air flow with gases or smoke after atomization inside the atomizer 22 passes through the spaces among projections 284 to come into the mouth of the user via the venthole 287 and the opening 288.

One end of the atomizer 22 is installed onto the power supply output terminal of the cigarette rod 10. In this embodiment, diameter of the atomizer 22 is specially designed as 5 mm-7 mm to adapt to the through hole 254 of the simulated filter 25. The shape of the container 281 of the liquid chamber 28 is also corresponding to the through hole 254 of the simulated filter 25. The liquid chamber 28 can be partly engaged into the atomizer 22.

A columnar alloy sponge (not indicated on the Figs) is mounted within the atomizer 22 along its axes.

Figure 5:
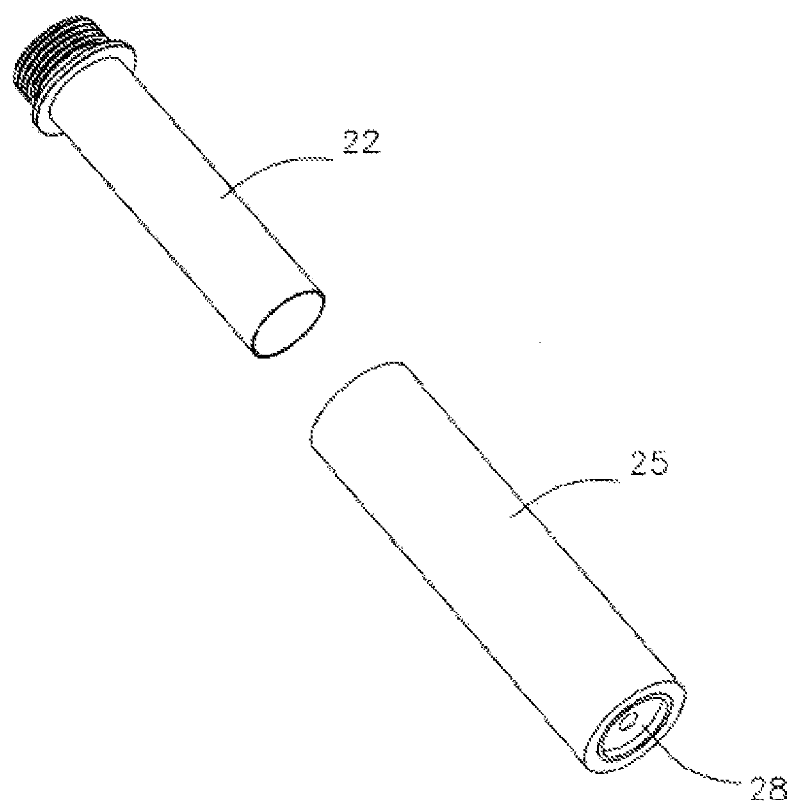
FIG. 5 is an assembly diagram for simulated cigarette mouthpiece before it is in use.

Please refer to FIG. 5, in assembly, the liquid chamber 28 is mounted within one end of the through hole 254 of the simulated filter 25, so the liquid chamber 28 and the simulated filter 25 is assembled together and forms One-piece structure. When in use, align the simulated filter 25 integrated with the liquid chamber 28 with the atomizer 22, and then press the simulated filter 25 to cover it on the atomizer 22. At this moment, part of front end of liquid chamber 28 inside the simulated filter 25 as corresponding to the narrower portion of its protrusion 284 is accommodated into one end of the atomizer 22, and the broader portion of each protrusion 284 is locked on the edge of the atomizer 22. Once the sealing membrane 30 on the end of liquid chamber 28 is broken under the extrusion of the columnar alloy sponge inside the liquid chamber 28, liquid in the container 281 will gradually leak out and permeate into the columnar alloy sponge. Meanwhile, the grooves 283 as provided on the outerwall of liquid chamber 28 can prevent leakage of liquid. When the user sucks the simulated filter 25 with lips, the electronic substitute cigarette is electrified and then enters into working state. Liquid inside the columnar alloy sponge will be gradually atomized by the atomizer 22, then air, gases or smoke flows into space between the protrusions 284 and simulated filter 25, and then passes through the square venthole 287 and the round opening 288, and finally gets into mouth of the user.

The simulated filter 25 integrated with the liquid chamber 28 is one-off product, which can be plugged out from the atomizer 22 and discarded with the liquid chamber 28 once liquid inside the liquid chamber 28 is used up. After that, a new simulated filter integrated with a new liquid chamber is to be covered on the atomizer, which is clean for use and convenient for replacement. The user can remove a simulated filter with a liquid chamber at any moment then install a new one for replacing.

As different from liquid supply mode of existing e-cigarette, there is no sponge in the liquid chamber in the present invention, in which, the liquid chamber is fully filled with liquid. Liquid inside the liquid chamber can fully flow into to the atomizer during use. As the liquid chamber is free of sponge and residual liquid, it is favorable for material saving.

Said simulated filter 25 not only can be made of filter mouthpiece materials of common real cigarette, but also other soft materials with comfortable tactility, such as filler of artificial fiber in addition to filter mouthpiece for common cigarettes. These kinds of soft materials can be wrapped with tobacco paper for common real cigarette.

Liquid inside the liquid chamber can be cigarette liquid simulating the taste of true cigarette or other liquids for medical treatment or nutrient solution which can be atomized.

The firelight simulating device 15 on the end of cigarette rod 10 comprises at least a LED flashing light and transparent or translucent decorating materials covered outside, such as an artificial diamond, crystal or painted glass. Accompanied by flash of the LED flashing light, it can give out colorful light through such decorating materials.

Electronic substitute cigarettes in accordance with the present invention integrate atomizer and liquid chamber in the simulated filter, of which, dimension and profile are similar to that of the true cigarette. It can increase the true tactility like conventional smoking and gives user a feeling of smoking true cigarette. User can control the smoking frequency through capacity control of the liquid chamber. Furthermore, the simulated filter of this invention can be replaced at any moment, for hygienic purposes and cleanness.

What is claimed is:

1. An electronic substitute cigarette comprising:

a cigarette rod comprising a battery and an electronic circuit; and a simulated cigarette mouthpiece comprising a simulated filter, a liquid chamber and an atomizer;

wherein the simulated filter comprises a main body and a through hole;

the liquid chamber comprises a sealing membrane for sealing a container of the liquid chamber and is mounted into one end of the through hole of the simulated filter forming a simulated filter with the integrated liquid chamber; and the atomizer is attachable to the simulated filter with the integrated liquid chamber and comprises a columnar alloy sponge, when the simulated filter with the integrated liquid chamber is engaged with the atomizer, the sealing membrane is broken by the columnar alloy sponge, and liquid in the container permeates into the columnar alloy sponge to be atomized by the atomizer.

2. The electronic substitute cigarette as claimed in claim 1, wherein the atomizer is connected with a power output terminal of the electronic substitute cigarette.

3. The electronic substitute cigarette as claimed in claim 1, wherein the liquid chamber and its sealing membrane are made of non-rigid materials.

4. The electronic substitute cigarette as claimed in claim 1, wherein at least one protrusion is extended from a sidewall of the container.

5. The electronic substitute cigarette as claimed in claim 4, wherein each protrusion comprises a first portion and a second portion narrower than the first portion, the first portion of each protrusion supports against an interior wall of the simulated filter, and spaces between the protrusions and the simulated filter let airflow overpass.

6. The electronic substitute cigarette as claimed in claim 5, wherein part of a front end of the liquid chamber, corresponding to the second portion of its protrusion, is accommodated into one end of the atomizer.

7. The electronic substitute cigarette as claimed in claim 1, wherein at least one groove is designed in a sidewall of the container for preventing liquid from leaking out.

8. The electronic substitute cigarette as claimed in claim 1, wherein said liquid chamber further comprises a base comprising a support portion and a plate, the plate engaged into the tail end of the through hole, at least one venthole designed in the support portion, an opening designed in the plate, and the vent hole and the opening connected each other to let airflow overpass.

9. The electronic substitute cigarette as claimed in claim 1, wherein said atomizer is adapted to the through hole of the simulated filter.

10. The electronic substitute cigarette as claimed in claim 1, wherein said liquid chamber is available for perfusion of 0.05ml-1.00m1 liquid.

11. The electronic substitute cigarette as claimed in claims 1, wherein the simulated filter integrated with the liquid chamber is an one-off product, which can be plugged out from the atomizer and discarded with the liquid chamber once liquid inside the liquid chamber is used up, after that, a new simulated filter integrated with a new liquid chamber is to be covered on the atomizer.

12. The electronic substitute cigarette as claimed in claim 1, wherein the simulated filter is soft.

13. The electronic substitute cigarette as claimed in claim 1 , wherein the simulated filter is made by rolling paper and filling soft materials within the rolling paper.

14. The electronic substitute cigarette as claimed in claim 1, wherein a firelight simulating device installed on one end of the cigarette rod comprises at least a LED flashing light.

15. The electronic substitute cigarette as claimed in claim 1, wherein the liquid chamber and its sealing membrane are made of PE, PC or PU.

16. The electronic substitute cigarette as claimed in claim 1, wherein the simulated filter is made by rolling paper and filling fiber, artificial fiber, cotton or sponge structure within the rolling paper.

* * * * *